United States Patent [19]

Gaines, Jr. et al.

[11] 4,325,263
[45] Apr. 20, 1982

[54] METAL SAMPLING APPARATUS

[76] Inventors: Frederick W. Gaines, Jr.; Ethel M. Gaines, both of 37451 Hunters Ridge Rd., Solon, Ohio 44139

[21] Appl. No.: 135,649

[22] Filed: Mar. 31, 1980

[51] Int. Cl.³ .............................................. G01N 1/12
[52] U.S. Cl. .................................................. 73/864.55
[58] Field of Search .................... 73/DIG. 9, 425.4 R, 73/864.53, 864.55; 164/4; 249/DIG. 4

[56] References Cited

U.S. PATENT DOCUMENTS 3,583,236  6/1971  Taylor ............................... 73/864.55
3,994,172  11/1976  Kelsey ............................ 73/425.4 R
4,010,649  3/1977  Falk ................................ 73/425.4 R

FOREIGN PATENT DOCUMENTS 1235306  6/1971  United Kingdom ........... 73/DIG. 9

Primary Examiner—S. Clement Swisher
Attorney, Agent, or Firm—Woodling, Krost & Rust

[57] ABSTRACT

A metal sampling apparatus including a cylindrically shaped mold having a closed end and an open end. The open end of the mold is closed by flat plate member. The apparatus is utilized to obtain a generally cylindrically-shaped sample of molten metal for testing and other purposes.

9 Claims, 9 Drawing Figures

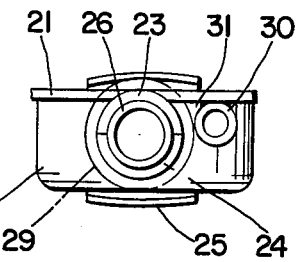
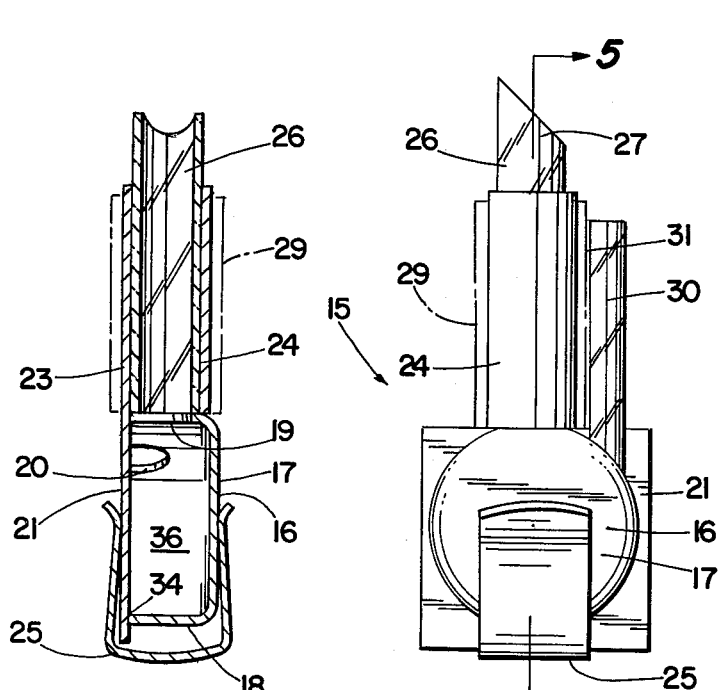
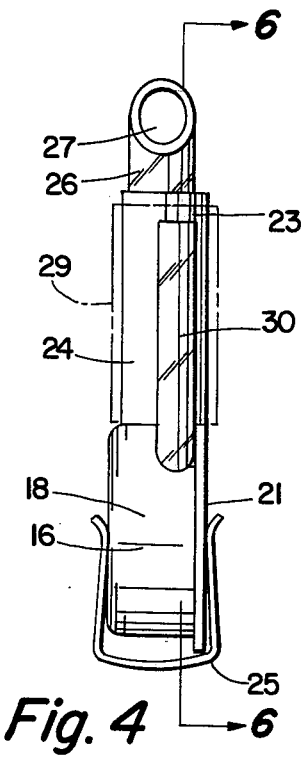
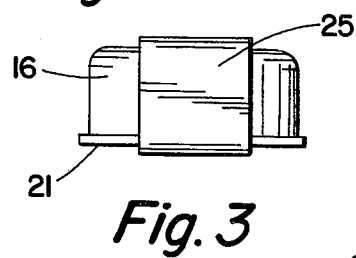
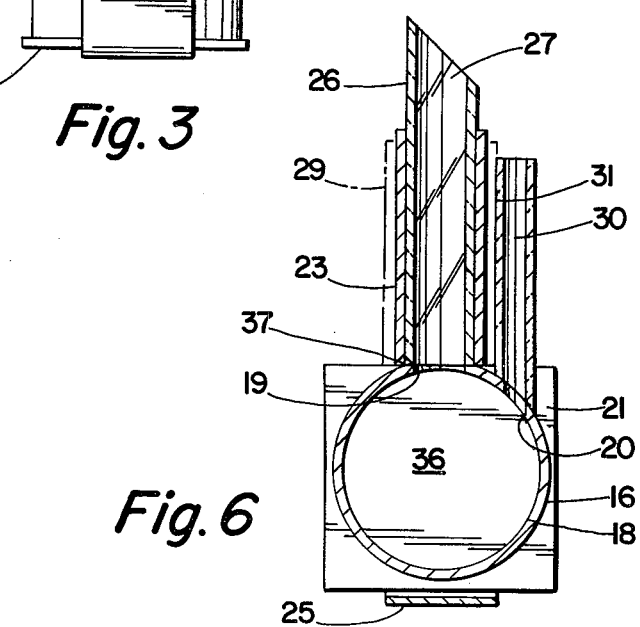

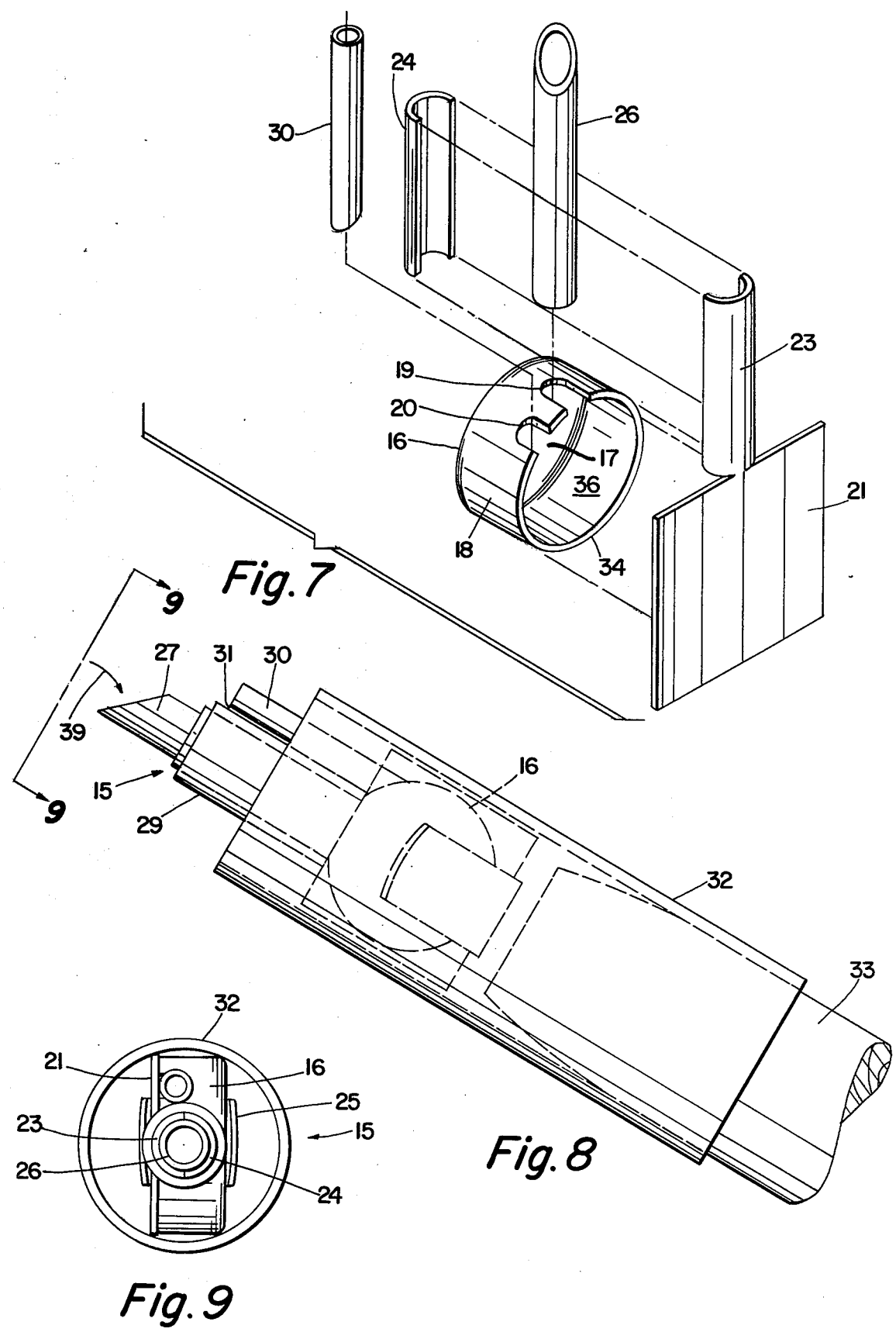

METAL SAMPLING APPARATUS

The metal sampling apparatus of the present invention is directed toward creating samples of a molten metal for analytical testing and other purposes. The apparatus is capable of use in preparing samples of other than molten metals; however, this is the primary purpose of the present invention.

The prior art includes metal sampling devices which comprise molds formed of two symmetrical banjo-shaped half molds joined at a central seam. Examples of the prior art can be found in U.S. Pat. Nos. 3,859,857; 3,897,689; and 4,002,072. The devices disclosed in these patents are not totally satisfactory because they are difficult to assemble and they also do not produce samples which are consistent. In use of the prior art devices just referred to, many times several samples must be taken because of faulty assembly of the devices resulting in shifting of the mold parts under pressure with resultant leakage. Samples which are produced in these prior art devices often need excessive grinding or machining in order to be of a consistent size and shape so that they can be used in conventional testing equipment.

The prior art also comprises one piece sand molds; however, these have not proven to be satisfactory in that they are difficult to make. In the use of sand molds it is practically impossible to cleanly separate the samples produced from the mold itself. The sand in this type of mold has a tendency to contaminate the metal samples that are produced which in turn tends to damage testing apparatus.

U.S. Pat. Nos. 3,994,172 and 4,010,649 also form part of the prior art and disclose sample molds which include a pipe-like opening closed on opposite sides by flat plates. These devices are quite unsatisfactory because their complicated structure makes them difficult to assemble and the structure itself creates substantial edge seams and impedes the removal of metal samples from the devices.

The metal sampling apparatus of the present invention devotes itself to overcoming the difficulty in the prior art and specifically the difficulties which have been referred to hereinabove. The apparatus of the present invention is not critical in its assembly in the that the mold parts of the apparatus can shift relative to each other without changing the shape of the metal sample that is produced. An advantage of the present apparatus is that it is not necessary to bond the various parts of the apparatus together with copious amounts of refractory cement.

The apparatus of the present invention is capable of producing metal samples of consistent size and shape without the necessity of grinding or machining the samples and therefore obviates delaying further processing of the samples until a minute inspection of the sample has been accomplished. The present apparatus is highly advantageous in that it is a very simple and easy matter to separate the sample produced with the apparatus.

The apparatus also produces a metal sample which has very minimal seam residue and any seam residue that is produced is confined to an edge where it is easily removed.

Other objects and a fuller understanding of the present invention may be had by referring to the following description and claims taken in conjunction with the accompanying drawings in which:

FIG. 1 is a front elevational view of the apparatus of the present invention;
FIG. 2 is a top view of FIG. 1;
FIG. 3 is a bottom view of FIG. 1;
FIG. 4 is a view taken from the right side of FIG. 1;
FIG. 5 is a view taken generally along the line 5—5 of FIG. 1;
FIG. 6 is a view taken generally along the line 6—6 of FIG. 4;
FIG. 7 is an exploded isometric view of some of the major components of the apparatus of the present invention and illustrated in this manner for greater ease of understanding of the structure;
FIG. 8 is a view illustrating the apparatus of the present invention as inserted into one end of a cylindrical holder which holder in turn is carried by an extension rod or pole; and
FIG. 9 is a view taken generally along the line 9—9 of FIG. 8.

The metal sampling apparatus of the present invention is indicated generally in the drawings by the reference numeral 15. As mentioned hereinabove the apparatus has for its purpose the collecting of a sample of molten metal which sample is of a convenient size and shape for the purpose of performing various tests thereupon to determine the quality of the main batch of molten metal from which the sample is taken. The invention is shown in all the drawings; however, FIG. 7 gives a good visual impression of some of the basic components of the apparatus.

It will be seen that the apparatus includes a generally cylindrically shaped mold member 16 which has an annularly extending sidewall 18 and an end wall 17 which is formed integrally with sidewall 18. The sidewall 18 terminates in an edge 34 which edge defines an opening to the mold member 16 and the edge is located substantially in a single plane.

Wall means are provided in the sidewall 18 and serve to define the first and second slots 19 and 20 respectively which extend from the edge 34 into the sidewall toward the end wall 17 as illustrated in the drawings and particularly in FIG. 7.

A substantially flat closure plate member 21 is provided and engages the edge 34 of the mold member 16 to define a mold cavity identified by reference numeral 36. The first and second slots 19 and 20 form first and second adjacent openings to the mold cavity 36.

The structure which has just been described can be constructed of any suitable material that can withstand the temperature of the molten metal to be sampled. Typical materials which are satisfactory include steel, powdered metal, ceramics and graphite. In the preferred embodiment which is disclosed herein the structure of these recited elements is steel.

A first semi-circular inlet tube support member 23 is integrally connected to the plate member 21 and is provided with a first end portion 37 which engages the sidewall 18 of the mold member 16 at the first slot 19. (See FIG. 6) Means are provided for holding the mold member 16 and the flat closure plate 21 with its associated tube support portion 23 in the position illustrated best in FIGS. 1, 4 and 5 and this means comprises a U-shaped spring member 25 associated with these parts as illustrated in the drawings.

A separate second semi-circular inlet tube support member 24 is located in facing engagement with the first inlet tube support as shown in the drawings and these two mentioned inlet tube supports 23 and 24 form a support opening therebetween. The second inlet tube support member has a first end portion which also engages the sidewall 18 of mold member 16 at the first slot 19. An inlet tube 26 is located in the support opening which is formed by members 23 and 24 and at one end is in engagement with the first slot 19 and is in communication with the first opening defined by the first slot and the mold cavity 36. An assembly tube 29 (shown in full lines in FIG. 8 and otherwise in dot-dash lines) preferably made of cardboard or other paper material surrounds the first and second inlet tube supports 23 and 24 to hold them in position relative to each other so as to enable them to support the inlet tube 26. It is preferred that the inlet tube 26 be constructed of quartz material; however, it is only necessary that the material of construction be of such a nature that it can stand the temperature of the product to be received therethrough. The inlet tube 26 is provided with a beveled end 27 for ease in receiving molten metal thereinto which molten metal travels to the mold member 16 to produce the metal sample. The inlet tube 26 at its end opposite end 27 where it engages the first opening into the mold cavity may be bonded in this position by a refractory cement; however, under normal circumstances, the fit of the inlet tube 26 at this point is sufficient to prevent any leakage which would tend to damage the sample being produced.

An outlet tube or air vent tube 30 is provided and has one end portion in communication with the opening defined by the second slot 20. The outlet tube 30 is preferably held in position by the use of cement or glue 31 which is located between the tube 30 and the assembly tube 29. In like fashion a refractory cement may be provided between the end of outlet tube 30 and the opening to the mold cavity 36 which is provided at the second slot 20; however, under normal circumstances, this is not necessary. Under many circumstances of use of the apparatus of the present invention the outlet tube 30 is not totally necessary; however, under most circumstances, it is desirable because it provides for the escape of gas from the mold cavity and assists in providing a more dense and sound sample. The construction of outlet tube 30 is preferably of high temperature glass; however, any suitable material may be utilized. It will be apparent to those skilled in the art that the temperatures that must be withstood by outlet tube 30 are substantially less than inlet tube 26 due to the cooling that has taken place by the molten metal before it reaches outlet tube 30.

The apparatus of the present invention as shown in its assembled condition in FIGS. 1–6 is in condition to perform its ultimate function. In order to properly handle the apparatus 15 it is preferably that some type of assembly be used so that a workman can conveniently manipulate the beveled end 27 of inlet tube 26 into a stream of molten metal to extract a sample as desired. To accomplish this end a holder tube 32 is provided as shown in FIG. 8 which tube is preferably made of a heavy cardboard material. The holder tube is open at both ends and has an inside diameter which is approximately equal to the width of the flat closure plate member 21. This enables the apparatus 15 to be simply wedgingly inserted into one end of the holder tube 32 whereby the wedging or frictional engagement between the two members holds the mold member 16 of the apparatus 15 and associated structure in place. A rod or extension member 33 is insertable into the other end of the holder tube 32 and may be of any desired length so that the entire assembly can be held by a workman at an end of rod 33 remote from the holder tube 32. The workman may easily manipulate the apparatus to insert the beveled end 27 of inlet tube 26 into a stream of molten metal which molten metal is flowing generally in the direction of arrow 39 seen in FIG. 8. It will be apparent to those skilled in the art that the molten metal flows through inlet tube 26 through the opening formed by the first slot 19 in sidewall 18 and into mold cavity 36 of mold member 16. Air and other gases are forced from the mold cavity 36 through outlet tube 30 as the cavity fills with molten metal. The metal sprue that may form in the outlet tube 30 can be removed from the finally finished sample as another portion upon which tests may be conducted.

The metal sample that is produced in the present apparatus may be quickly and conveniently removed from the assembly by the simple expedient of disassembling the spring member 25, assembly tube 29, mold member 16, closure plate member 21 and attached tube support 23 and the separate tube support 24 from each other. The metal sample is conveniently exited the space of the mold member defined by the sidewall 18 and the end wall 17. The referred to parts may be quickly and conveniently reassembled for the preparation of another sample.

It will be apparent from a review of the structure which has been disclosed and described herein that the assembly of the apparatus of the present invention is not critical in that the closure plate member 21 need not be precisely located with respect to mold member 16 and a certain amount of shifting between these two parts will not result in a defective sample. The engagement of the lower end of tube support 23 adjacent the first slot 19 is a part of the structure which results in convenient assembly of the various parts and tends to keep the closure plate member and the mold member in a related position with respect to each other. The same is true of the engagement of the second tube support 24 with the first slot 19. The replacement of the assembly tube 29 when it is constructed of cardboard or other paper material is accomplished in a relatively economic fashion because the cost of such materials is relatively low and the same is true when damage results to the holder tube 32 when it is constructed of cardboard or other similar material.

It will also be understood by those skilled in the art that the mold member may be other than cylindrical in shape. The annularly extending sidewall may define many shapes, for example, rectangular, triangular and hexagonal which shapes will function is essentially the same manner as the circular or cylindrical shape specifically disclosed herein.

It will be appreciated that regardless of the shape of the mold it is interchangeable with the other components disclosed herein. The use of different mold shapes does not alter the cost of manufacturing and the shape and size of the mold member can vary to suit a user's need within the outside dimensions of the flat closure plate member 21. Different shapes do not alter the cost of manufacture. The use of different mold shapes does not compromise the fact that consistent samples are obtained with the present apparatus without undesirable parting lines.

Although this invention has been described in its preferred form with a certain degree of particularity, it is understood that the present disclosure of the preferred form has been made by way of example only and that numerous changes in the details of construction and the combination and arrangement of parts may be resorted to without departing from the spirit and the scope of the invention as hereinafter claimed.

What is claimed is:

1. Apparatus for collecting a sample of a molten metal including in combination a mold member having an end wall and an annularly extending sidewall extending therefrom and terminating in an edge which edge is located substantially in a single plane, a substantially flat closure plate member engaging said edge of said annularly extending sidewall and in combination with said mold member defining a mold cavity, wall means in said sidewall forming an opening to said mold cavity, inlet conduit means communicating with said opening to said mold cavity, and spring clamping means holding said mold member and said flat closure plate in position relative to each other.

2. Apparatus as claimed in claim 1 wherein said wall means which form said opening to said mold cavity comprises a first slot in said edge of said annularly extending sidewall.

3. Apparatus for collecting a sample of a molten metal including in combination a generally cylindrically shaped mold member having an end wall and an annularly extending sidewall extending therefrom terminating in an edge which edge is located substantially in a single plane, wall means defining first and second slots in said annularly extending sidewall and each slot extending from said edge of said sidewall, a substantially flat closure plate member engaging said edge of said annularly extending sidewall and in combination with said mold member defining a mold cavity, said first and second slots forming first and second adjacent openings to said mold cavity, means holding said mold member and said flat closure plate member in position relative to each other, a semi-circular inlet tube support member integrally connected to said plate member and having a first end portion engaging said mold member sidewall at said first slot, an inlet tube extending adjacent said semi-circular inlet tube support member and communicating with said first opening to said mold cavity, a cardboard assembly tube member surrounding said inlet support member and said inlet tube, and holding the same in position relative to each other, an outlet tube communicating with said second opening to said mold cavity and being held in position by adhesive between said outlet tube and said cardboard assembly tube member, a cardboard holder tube having an open end portion and surrounding said mold member and flat closure plate member with said inlet tube and outlet tube extending from said open end portion, said flat closure plate member being of a size to engage the inner wall of said holder tube and be held in place by a wedging action.

4. Apparatus for collecting a sample of a molten metal including in combination a generally cylindrically shaped mold member having an end wall and an annularly extending sidewall extending therefrom terminating in an edge which edge is located substantially in a single plane, wall means defining first and second slots in said annularly extending sidewall and each slot extending from said side edge of said sidewall, a substantially flat closure plate member engaging said edge of said annularly extending sidewall and in combination with said mold member defining a mold cavity, said first and second slots forming first and second adjacent openings to said mold cavity, means holding said mold member and said flat closure plate member in position relative to each other, a semi-circular inlet tube support member integrally connected to said plate member and having a first end portion engaging said mold member sidewall at said first slot, an inlet tube extending adjacent said semi-circular inlet tube support member and communicating with said first opening to said mold cavity, an assembly tube member surrounding said inlet tube support member and said inlet tube, and holding the same in position relative to each other, and an outlet tube communicating with said second opening to said mold cavity.

5. The apparatus of claim 3 or 4 and further including a second semi-circular inlet tube support member in facing engagement with said semi-circular inlet tube support member and forming a support opening therewith, said second inlet tube support member engaging said mold member sidewall at said first slot, and wherein said inlet tube extends adjacent and between said inlet tube support means and said second inlet tube support means, residing in said support opening, and wherein said assembly tube member surrounds both inlet tube support means and said inlet tube means.

6. Apparatus for collecting a sample of a molten metal including in combination a mold member having an end wall and an annularly extending sidewall extending therefrom and terminating in an edge which edge is located substantially in a single plane, a substantially flat closure plate member engaging said edge of said annularly extending sidewall and in combination with said mold member defining a mold cavity, said annularly extending sidewall having a slot in said edge thereof and said slot forming an opening to said mold cavity, and further including an inlet tube support member connected to said flat closure plate member, an inlet tube member extending adjacent said inlet tube support member, an assembly member holding said inlet tube member to said inlet tube support member and in communication with said opening to said mold cavity, and means holding said mold member and said flat closure plate in position relative to each other.

7. Apparatus as claimed in claim 6 wherein said inlet tube support member is integrally connected to said flat closure plate, and further including a second inlet tube support member cooperating with said first mentioned inlet tube support member to support said inlet tube member, and wherein said assembly member surrounds said two mentioned inlet tube support members and said inlet tube member to hold said three mentioned members together.

8. Apparatus as claimed in claim 7 wherein said flat closure plate is generally rectangular in configuration with the distance between two sides of the rectangular configuration being of such size as to be wedgingly received in the end of a cardboard tube with said inlet tube member extending therefrom to receive a flow of molten metal.

9. Apparatus for collecting a sample of molten metal including in combination a mold member having an end wall and an annularly extending sidewall extending therefrom and terminating in an edge which edge is located substantially in a single plane, a substantially flat closure plate member engaging said edge of said annularly extending sidewall and in combination with said mold member defining a mold cavity, said annularly extending sidewall having first and second slots in said edge thereof, said first and second slots forming first and second openings to said mold cavity, and further including inlet conduit means communicating with said first opening to said mold cavity, an outlet tube member connected to said second opening to said mold cavity, and means holding said mold member and said flat closure plate in position relative to each other.

* * * * *